(12) United States Patent
Dijkman

(10) Patent No.: US 11,046,604 B2
(45) Date of Patent: Jun. 29, 2021

(54) PROCESS FOR THE TREATMENT OF WASTEWATER CONTAINING ORGANIC MATERIAL AND AMMONIA

(71) Applicant: PAQUES I.P. B.V., Balk (NL)

(72) Inventor: Hendrik Dijkman, Balk (NL)

(73) Assignee: PAQUES I.P. B.V., Balk (NL)

(*) Notice: Subject to any disclaimer, the term of this patent is extended or adjusted under 35 U.S.C. 154(b) by 135 days.

(21) Appl. No.: 16/317,451

(22) PCT Filed: Jul. 14, 2017

(86) PCT No.: PCT/EP2017/067906
§ 371 (c)(1),
(2) Date: Jan. 11, 2019

(87) PCT Pub. No.: WO2018/011413
PCT Pub. Date: Jan. 18, 2018

(65) Prior Publication Data
US 2019/0225519 A1    Jul. 25, 2019

(30) Foreign Application Priority Data

Jul. 15, 2016 (EP) .................................. 16179754

(51) Int. Cl.
C02F 3/34 (2006.01)
C12P 7/62 (2006.01)
C02F 3/30 (2006.01)

(52) U.S. Cl.
CPC ............. *C02F 3/341* (2013.01); *C12P 7/625* (2013.01); *C02F 3/302* (2013.01); *C02F 3/307* (2013.01); *C02F 2209/02* (2013.01); *C02F 2209/06* (2013.01); *C02F 2209/14* (2013.01); *C02F 2209/15* (2013.01); *C02F 2209/245* (2013.01); *C02F 2305/06* (2013.01)

(58) Field of Classification Search
CPC ...... C02F 3/341; C02F 3/302; C02F 2209/02; C02F 2209/06; C02F 2209/14; C02F 2209/15; C02F 2209/245; C02F 2305/06; C02F 3/307; C12P 7/625
See application file for complete search history.

(56) References Cited

U.S. PATENT DOCUMENTS 8,030,021 B2    10/2011    Criddle et al.

FOREIGN PATENT DOCUMENTS

| EP | 2163525 A1 | 3/2010 |
|---|---|---|
| WO | WO-00/05176 | 2/2000 |
| WO | WO 2008/046139 A1 | 4/2008 |
| WO | WO 2011/073744 A1 | 6/2011 |
| WO | WO-2014/102297 | 7/2014 |
| WO | WO-2014/171819 A1 | 10/2014 |
| WO | WO-2015/181083 | 12/2015 |

OTHER PUBLICATIONS

Frison et al., Environ. Sci. Technol., 2015, vol. 49, p. 10877-10885.*
Escudero et al., NIVA 6634-2014, May 2014, 22 pages of PDF.*
International Search Report issued in PCT/EP2017/067906, dated Sep. 20, 2017.
Written Opinion of the International Searching Authority issued in PCT/EP2017/067906, dated Sep. 20, 2017.
Innerebner et al., "Identification of anammox bacteria in a full-scale deammonification plant making use of anaerobic ammonia oxidation", Systematic and Applied Microbiology, 2007, vol. 30, Iss. 5, pp. 408-412 (5 pages).

* cited by examiner

*Primary Examiner* — Kade Ariani
(74) *Attorney, Agent, or Firm* — Foley & Lardner LLP

(57) ABSTRACT

Wastewater containing a significant level of dissolved readily biodegradable organic compounds matter, such as short-chain fatty acids, and ammonia can be efficiently treated to remove most or all of the organic compounds and the ammonia, with the production of microbial storage compounds such as polyhydroxylkanoates, by (i) subjecting the wastewater storage compound-accumulating microorganisms (SCAM) in the presence of oxygen, (ii) subjecting at least part of the resulting partly treated wastewater to ammonia-oxidising microorganisms (AOM) in the presence of oxygen and (iii) feeding a gas containing molecular carbon dioxide produced during step (ii) to step (i) so as to lower the pH in step (i).

18 Claims, 1 Drawing Sheet

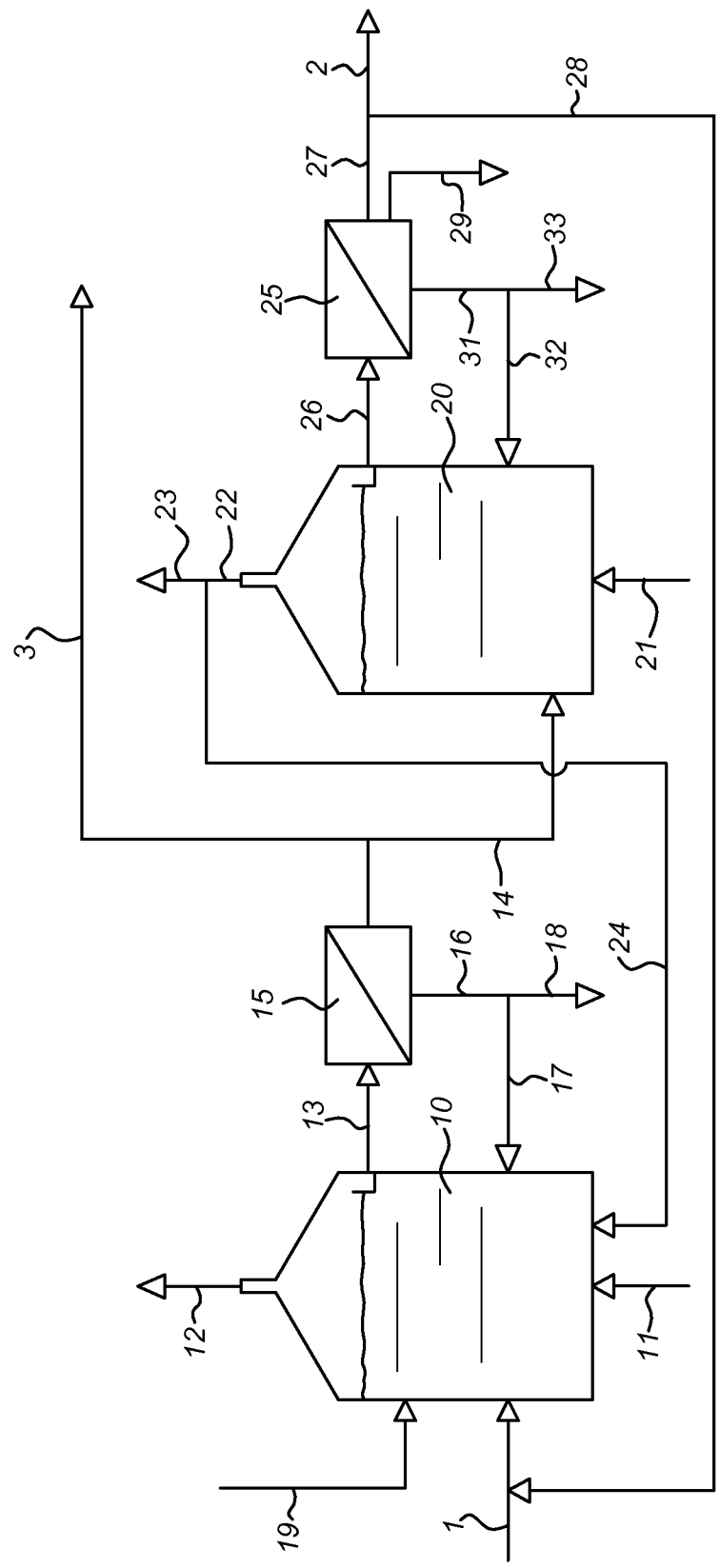

PROCESS FOR THE TREATMENT OF WASTEWATER CONTAINING ORGANIC MATERIAL AND AMMONIA

CROSS-REFERENCE TO RELATED APPLICATIONS

This application is the National Phase of International Patent Application No. PCT/EP2017/067906, filed Jul. 14, 2017, published on Jan. 18, 2018 as WO 2018/011413 A1, which claims priority to European Application No. 16179754.3, filed Jul. 15, 2016. The contents of these applications are herein incorporated by reference in their entirety.

FIELD OF THE INVENTION

The present invention relates to a process for treating wastewater containing readily biodegradable COD and ammonia, to produce a microbial storage compound (MSC), in particular a process for producing polyhydroxyalkanoate (PHA), using micro-organisms accumulating the microbial storage compound.

BACKGROUND ART

Processes for the production of PHA or other microbial storage compounds are known in the art and typically comprise cycles alternating a so-called "feast" phase wherein sludge comprising PHA-accumulating bacteria is fed with a substrate that comprises readily biodegradable organic compounds (so-called readily biodegradable chemical oxygen demand or RBCOD) with a so-called "famine" phase wherein the substrate is withheld from the bacteria. In the feast phase, the PHA-accumulating bacteria are converting RBCOD such as volatile fatty acids (VFA) to PHA. In the famine phase, the PHA accumulated in the bacteria is used as feed, resulting in selection of those bacteria that are capable of accumulating PHA or other bacterial storage compounds.

U.S. Pat. No. 8,030,021 (Leland Stanford Jr) discloses such a process in which mixed cultures of PHA-producing microbes convert VFA to PHA in a sequencing bioreactor with repeating cycles of feast-like conditions (excess feedstock—VFA—and limited nutrients—nitrogen, phosphorus etc.—), and famine-like conditions (excess nutrients and limited feedstock).

WO2015/181083 (Paques) discloses a PHA-producing process comprising subjecting wastewater to PHA-accumulating microorganisms in a two-stage PHA accumulation reaction in a first reactor, withdrawing part of the PHA-accumulating microbes after the first stages and subjecting these to famine conditions in a second reactor in parallel with the second-stage accumulation reaction.

Further processes for producing PHA are described e.g. in WO 2014/102297 and WO 2011/073744.

Innerebner et al., *Systematic and Applied Microbiology* 30 (2007) 408-412 disclose a single-stage, single-tank deammonification plant for treating ammonium-containing wastewater wherein ammonium is converted to nitrite by means of aerobically oxidising bacteria (AOB) and then ammonium and nitrite are converted to elemental nitrogen by means of anaerobically oxidising bacteria (frequently referred to as Anammox bacteria). Sludge is removed from the reactor and separated into two phases: a heavy phase mainly comprising Anammox bacteria and a light phase. Similar processes are described e.g. in WO 00/05176 and EP 2163525, wherein the light phase (non-granular sludge) is largely discharged and the heavy phase (granular sludge) is largely returned to the reactor. WO2014/171819 discloses a similar process performed at low temperatures (5-25° C.) involving careful control of hydraulic retention times and granular sludge retention times. WO 2008/046139 discloses a stage-wise biological process for reducing nitrogen and phosphorus levels in wastewater and for producing PHA in the same reactor.

SUMMARY OF THE INVENTION

According to the present invention, a process is provided in which MSC production and ammonia removal are combined in such a way that pH control using undesired levels of alkali and acid is minimised. This is achieved by returning $CO_2$-containing gas and/or liquid produced in the biological ammonia treatment stage to the preceding stage of biologically treating organic waste to produce MSC.

BRIEF DESCRIPTION OF THE DRAWINGS

The present invention will be discussed in more detail below, with reference to the attached drawing, which the FIGURE schematically illustrates an embodiment of the invention.

DETAILED DESCRIPTION

The present disclosure pertains to a process for producing a microbial storage compound (MSC) from a feed stream containing readily biodegradable chemical oxygen demand (RBCOD) and ammonia. The level of RBCOD is at least 250 mg/l, and the level of ammonia at least 20 weight % of the level of RBCOD. The process is further defined in appending claim 1, and preferred embodiments are defined in the dependent claims; it is to be understood that any combination of preferred embodiments constitutes a disclosure of a further preferred embodiment.

Typical feed streams to be treated are pH-neutral to high-pH streams rich in volatile fatty acids and dissolved ammonia such as effluents from leaching and removal of volatile fatty acids from green waste or certain condensate streams e.g. condensates from municipal sludge drying operations. The fact that these streams contain salts of ammonia and volatile fatty acids as major components results in a further increase in pH when the volatile fatty acids are converted to storage compounds like PHA. For stable operation of the biological process in the MSC production process, addition of acid is required to keep the pH below 9. The advantage of the process is that no external acid is required, which reduces operational cost and lowers salt concentration in the treated water. The required acid is liberated in a downstream nitrogen removal process where oxidation of ammonia lowers the pH and converts carbonate and bicarbonate to acidic carbon dioxide. By recycling at least part of the liberated carbon dioxide to the PHA production step, the pH in that step can be controlled to below pH 9 without the need for external acid to be added.

In the context of the present invention the following definitions apply:

"Microbial storage compounds" are compounds produced by microorganisms such as bacteria, moulds, and algae, for storing their surplus energy. The compounds include esters, polyesters, polythioesters, triglycerides (triacylglycerols), other fats and oils, and polysaccharides such as glycogen. Polyesters resulting from intermolecular esterification of hydroxy-carboxylic acids are an important class of microbial storage compounds, the most prominent ones being poly-hydroxyalkanoic esters, in particular poly-β-hydroxyalkanoic esters, such as poly-β-hydroxy-butyrate (PHB) and poly-β-hydroxyvalerate (PHV) having the formulae below, wherein n may range from tens to hundreds or even many thousands, as well as their copolymers.

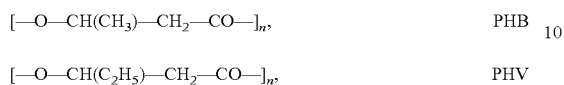

The poly-hydroxyalkanoic esters (or poly-oxyalkanoates) are commonly (and herein) referred to as poly-hydroxyalkanoate (PHA).

Triglycerides (triacylglycerols: RAG) having varying acyl groups, mainly C16-C18 are also important bacterial storage compounds.

"Chemical Oxygen Demand" (COD) refers to organic material that can be oxidised to smaller molecules, ultimately to carbon dioxide and water, and the term expresses the amount of oxygen that would be needed to fully oxidise the organic material in a given volume of waste-water.

"Biodegradable COD" refers to organic material in wastewater that can be assimilated for biomass growth and also expresses the amount of oxygen needed to fully oxidise the organic material in a given volume of wastewater.

"Readily Biodegradable Chemical Oxygen Demand (RBCOD)" refers to relatively small organic molecules that can be quickly assimilated by microorganisms as further illustrated below. Examples of such RBCOD include volatile fatty acids, also referred to as short-chain fatty acids, i.e. having up to 6 carbon atoms, as defined below, carbohydrates such as mono-saccharides and disaccharides, uronic acids, alcohols, polyols, ketones, and aldehydes, preferably alcohols, polyols, ketones, and aldehydes with up to six carbon atoms and combinations of two or more thereof. In other words, RBCOD refers to organic compounds having up to 6 carbon atoms per molecule and having at least one hydroxylic (C—OH) or ketonic (C=O) oxygen atom per molecule and at least one oxygen atom per four carbon atoms, preferably having carbon, hydrogen and oxygen atoms only, as well as disaccharides. The concentration of RBCOD can be determined by means of standardised methods of respirometry that determine the fraction of wastewater COD that is rapidly utilised when an aliquot of wastewater with a specified amount of biomass is pulse-fed with substrate under controlled conditions. An example of a suitable standardised method of respirometry is disclosed in M. Henze et al., *Activated Sludge Models ASM1, ASM2, ASM2d and ASM3*, IWA Publishing, London, 2000, p. 16-17; ISBN 1900222248.

"Volatile Fatty Acids" (VFA) refer to fatty acids having boiling points at ambient conditions of below 250° C. and/or having up to six carbon atoms per molecule, such as formic acid, acetic acid, propionic acid, butyric acid, isobutyric acid, valeric acid, isovaleric acid, and caproic acid, and hydroxy fatty acids such as lactic acid and keto fatty acids, which can be obtained by anaerobic digestion of organic waste material.

"Other Biodegradable Chemical Oxygen Demand (OBCOD)" refers to bio-degradable COD other than RBCOD, i.e. more complex and less accessible organic compounds, for example complex polysaccharides, fats and proteins, as well as organic compounds having relatively few oxygen-containing groups and relatively large hydrocarbon groups, such as long-chain fatty acids.

"Ammonia" includes azane (nitrogen trihydride, $NH_3$) and any of its ionised, including protonated ($NH_4^+$) forms, whether free or as a complex such as a salt; amounts of ammonia are expressed in weight of elemental nitrogen.

"RBCOD-depleted" and "ammonia-depleted" refer to a content of RBCOD and ammonia, respectively, which is significantly below the original level. In particular it means that the levels have been reduced by at least 40%, more in particular by at least 70%.

"Wastewater" refers to an aqueous stream comprising COD that needs to be treated before it can be reused or discharged to the environment. Wastewater for example includes process water, side-product or intermediate product streams from bio-based or other industries.

"Sludge" refers to any solid or solid-like material present in a reactor or its influent or effluent which can be separated from the liquid part of the reactor (or influent or effluent) by physical means, such as filters, (hydro) cyclones, settlers, centrifuges, membranes and the like. The sludge can comprise an organic part, which includes all biological material as well as non-soluble or not finely dispersible organic compounds, and an inorganic part, which includes non-soluble or not finely dispersible salts and other inorganic material. Thus, "dry organic sludge" comprises solid material, from which inorganic materials (salts, ash) and water and other liquids have been separated or have been taken into account in calculating product levels.

"Reactor stage" relates to a reactor content entity which is separated from another reactor content entity in space and/or time. For example, it can be a compartment or zone of a reactor which is partly or wholly physically separated (by a wall, a narrowing or another barrier) from another zone of the reactor. It can also be a separate reactor. Further, a reactor stage may be a reactor phase which has a different content, composition or set of conditions from another phase, in the same space, which follows or precedes the reactor stage (in a non-continuous process).

"Elements essential for growth" or "nutrients essential for growth" comprise the commonly known elements—other than the structural elements carbon, oxygen and hydrogen—, which the cell requires for proper growth. These includes macro-elements N, P, K and S, micro-elements Mg, Ca, Fe, and trace elements such as Mn, Mo, Zn, Co, Cu, Ni, B, Se, W, Cl, as well as vitamins. While any of the elements, including vitamins, can be used for controlling the growth of organisms, nitrogen and phosphorus can be advantageously used. Since nitrogen will typically not be limiting in the present process, phosphorus is the primary element for controlling microbial growth. The elements essential for growth can be provided in any conventional and appropriate, preferably water-soluble, form, e.g. phosphoric acid, phosphate salts, potassium, magnesium, calcium or iron salts (chloride, nitrate, acetate, etc.), sulfate salts, trace metal salts, vitamins or vitamin salts, etc.

"Hydraulic Retention Time" (HRT) is the average retention time of liquid (wastewater) in the reactor or reactor system under consideration. In a continuous operation, the HRT is equivalent to the effective volume of the reactor content divided by the volume of liquid added to (and discharged from) the reactor per time unit.

"Sludge Retention Time" (SRT) is the average retention time of total sludge in the reactor (system). It can be different from the HRT by partial separation and return of sludge. The SRT can also be defined as the time-averaged amount of sludge present in the reactor (kg dry solids) divided by the time-averaged amount of solids produced in the system and removed from the system (kg dry solids/h).

Similarly, "Granular Sludge Retention Time" (GSRT) and "Non-granular Sludge Retention Time" (NGSRT) are the average retention times of granular sludge and non-granular sludge, respectively, in a reactor of the present process.

In a preferred embodiment, the present process comprises:
(a) subjecting the feed stream to storage compound-accumulating microorganisms (SCAM) in the presence of dissolved oxygen, while adding carbon dioxide as necessary for maintaining a pH below 9, in one or more stages, to produce SCAM which contain MSC at a level of at least 50 wt. % based on dry weight of the organic part of the microorganisms, and RBCOD-depleted wastewater;
(b) separating at least a part of the SCAM after step (a) from the RBCOD-depleted wastewater;
(c) optionally returning a part of the separated SCAM to step (a);
(d) subjecting RBCOD-depleted wastewater produced in step (a) to ammonia-oxidising micro-organisms (AOM) to produce RBCOD-depleted and ammonia-depleted wastewater, and a gas containing molecular carbon dioxide;
(e) feeding a part of said gas containing carbon dioxide to step (a);
(f) harvesting at least a part of the SCAM separated in step (b), and
(g) optionally isolating MSC from the harvested SCAM.

In an especially preferred, exemplary embodiment, the present process comprises:
(a) subjecting the feed stream, containing organic compounds with up to 6 carbons and at least one hydroxylic or ketonic oxygen per molecule, as RBCOD, to PHA-accumulating micro-organisms (PHA-AM) in the presence of dissolved oxygen, while adding carbon dioxide as necessary for maintaining a pH below 9, in one or more stages, while limiting the level of at least one element essential for growth, such as phosphorus, to produce PHA-AM which contain PHA at a level of at least 50 wt. % based on dry weight of the organic part of the microorganisms, and RBCOD-depleted wastewater;
(b) separating at least a part of the PHA-AM containing PHA produced in step (a) from the RBCOD-depleted wastewater;
(c) optionally returning a part of the separated PHA-AM to step (a);
(d) subjecting RBCOD-depleted wastewater produced in step (a) to ammonia-oxidising micro-organisms (AOM) to produce RBCOD-depleted and ammonia-depleted wastewater, and a gas containing molecular carbon dioxide;
(e) feeding a part of said gas containing carbon dioxide to step (a);
(f) harvesting at least a part of the PHA-AM separated in step (b), and:
(g) isolating PHA from the harvested PHA-AM.

In step (a) of the present process, RBCOD, as defined above, is partly or even largely converted to microbial storage material, such as polyhydroxyalkanoate, in one or more stages or one or more reactors as further described below. In step (d), at least part of the resulting RBCOD-depleted stream still containing ammonia, is treated to significantly lower the level of ammonia by biological oxidation. Also residual RBCOD and OBCOD can be oxidised in this step (d).

Step (a) of the present process may comprise any biosystem that converts RBCOD to microbial storage compound (MSC), in particular to polyhydroxyalkanoate (PHA) in the presence of (dissolved) molecular oxygen. Thus step (a) typically is an aerated process stage. The concentration of dissolved oxygen in step (a) is preferably from 1.0 to 3.0 mg/L.

MSC-accumulating microorganisms (SCAM) for use in step (a) are well known in the art. PHA-accumulating bacteria and other micro-organisms capable of accumulating microbial storage compounds such as triacylglycerol-accumulating bacteria are typically present in non-axenic cultures of micro-organisms such as found in soil, natural water or mixed biomass samples. They can also be isolated or enriched from common municipal wastewater plants. The PHA-accumulating bacteria can belong to various genera such as *Alcaligenes* (e.g. *A. latus*), *Ralstonia* (e.g. *R. eutropha*), *Cupriavidus* (e.g. *C. necator*), *Chromatium* (e.g. *C. vinosum*), *Mycobacterium*, *Bacillus*, *Pseudomonas*, *Thauera*, etc. They may specifically or non-specifically grow on various carbon sources such as glucose, methanol, ethanol, acetate and/or other fatty acids. See e.g. Tan G-Y.A. et al. *Polymers* 2014, 6, 706-754; Huang Y-T. et al. *J. Microbiol. Biotechnol.* 2012, 22, 1141-47. Particularly useful are bacteria of the genus *Plasticicumulans*, such as *P. acidivorans* (acetate-consuming) and *P. lacatativorans* (lactate-consuming), see e.g. Jiang et al. Int. *J. Systematic Evolutionary Microbiology* 2011, 61, 2314-2319, Tam is et al. *J. Biotechnology* 2014, 192, 161-169. TAG-accumulating microorganisms can belong to various genera such as *Streptomyces*, *Nocardia*, *Rhodococcus*, *Mycobacterium*, *Dietzia* and *Gordonia*. Particularly high levels of TAG can e.g. be produced by *Rhodococcus* species such as *R. opacus*. See e.g. Brigham et al. *J. Microbial Biochem. Technol.* 2011, S3.

In step (a) (or in the first stage (a1) thereof as described below), preferably at least one element which is essential for growth is limited so as to allow sufficient carbon to be incorporated into the microorganisms as MSC rather than being used for growth. Most conveniently, the limiting element comprises phosphorus. Preferably, the weight ratio, on element basis, of phosphorus to RBCOD-carbon in step (a) ($P_{a1}/C_a$) is below 1/100, more preferably below 1/125, down to e.g. 1/5000, preferably down to 1/2400. As a rough guide, the amount of RBCOD-carbon is about 1/3 of the amount of RBCOD (expressed in oxygen consumption), so the weight ratio of phosphorus to RBCOD in step (a) is below about 1/33, preferably below about 1/42, down to about 1/1700, preferably down to about 1/800.

In case the incoming wastewater has phosphorus levels which exceed the levels needed for controlling growth versus MSC accumulation, phosphorus, as phosphate, can be partly removed from the wastewater by a pretreatment in which magnesium is added to the wastewater and precipitated struvite (ammonium magnesium phosphate) is separated from the wastewater prior to step (a). Alternatively, or additionally, the ratio of phosphorus over carbon (or phosphorus over RBCOD) can be lowered by adding RBCOD, as described below.

If the limiting element comprises another element, the level thereof can be determined by the skilled person, on the basis of the known composition and elemental needs of bacteria. For example, the limiting levels of sulfur and iron can be taken at 2 times and 20 times, respectively, lower than the phosphorus level. Thus, by way of example, the weight ratio, on element basis, of sulfur or iron to RBCOD-carbon in step (a) ($S_{a1}/C_a$; $Fe_{a1}/C_a$) is preferably below 1/200 (S) or 1/2000 (Fe), more preferably below 1/250 (S) or 1/2500 (Fe), down to e.g. $1/10^4$(S) or $1/10^5$ (Fe), preferably down to 1/4800 (S) or 1/48,000 (Fe). The skilled person will be able to determine the limiting levels of other elements including trace elements and vitamins, should one of these be chosen for ensuring limited growth, by suitable routine experimentation involving varying levels of the element or vitamin in question. Essential elements which are not used at a growth-limiting level, are often already present in the wastewater in sufficient amounts or can be supplied if necessary, to achieve non-limiting levels. Common and commercially available element mixtures contain the various elements at the required relative levels.

In a particular embodiment, step (a) comprises two reactor stages. In stage (a1), the feed stream is subjected to SCAM in the presence of dissolved oxygen and with limitation of one or more nutrients which are essential for growth, such as phosphorus, so as to reduce the level of RBCOD to store MSC in the SCAM. In stage (a2) downstream of stage (a1), nutrients which are essential for growth, preferably including phosphorus, are supplied to the stream having a reduced RBCOD content so as to allow the microorganisms to grow while avoiding complete consumption of the stored MSC. Stages (a1) and (a2) can be operated in series, either in time or in place (two reactors or reactor compartments). Alternatively, stage (a2) can be operated as a side stream, returning grown SCAM to stage (a1).

In stage (a2), the amount of phosphorus supplied divided by the amount of RBCOD-carbon supplied in stage (a1) ($P_{a2}/C_a$) is preferably below 1/60, down to e.g. 1/500, more preferably below 1/75, even more preferably below 1/100, preferably down to 1/375. The levels of other elements essential for growth are at least the corresponding lower levels, unless one of these other elements is used as a decisive or limiting factor, in which case its lower level applies and phosphorus is above such a lower level.

In step (a), or in steps (a1) and (a2), the pH is preferably kept between 7 and 9, more preferably between 8.3 and 8.7. The level of dissolved oxygen is preferably between 0.5 and 4, more preferably between 1.0 and 3.0 mg/L. The temperature is preferably kept within the range of from 10 to 50° C., more preferably of from 20 to 40° C., and the conductivity is preferably in the range of from 0 to 20 mS/cm.

The time periods of stages (a1) and (a2) are preferably between 0.5 and 8 h, more preferably between 1 and 6 h for stage (a1) and between 0.1 and 6 h, more preferably between 0.2 and 3 h, for stage (a2). The hydraulic retention times (HRT) have corresponding preferences. The total sludge retention time (SRT) in step (a), or in the combined steps (a1) and (a2), is preferably between 6 and 72 h, more preferably between 12 and 48 h. The combination of the applied SRT, ammonia concentration, level of nutrient limitation and pH and temperature prevents the biological oxidation of ammonia in step (a).

In a preferred embodiment, a part of the RBCOD-depleted and ammonia-depleted waste-water produced in step (d) can be recycled to step (a) so as to reduce the concentration of ammonia in step (a) and to further lower the pH by recycling dissolved carbon dioxide. This optional recycle is especially relevant for streams containing very high ammonia concentrations in the feed stream. It is preferred to keep the total ammonia concentrations in step (a) below 1000 mg/l at pH 9 and a temperature of 30° C. or below 3000 mg/l at pH 8.5 and a temperature of 30° C.

In step (b), at least a part of the storage compound containing microorganisms (SCAM) containing MSC produced in step (a) is separated from the RBCOD-depleted wastewater using conventionally known separators, inside or outside the reactor (or one of the reactors) of step (a). Preferably, essentially all of the SCAM containing MSC is separated from the effluent of step (a). In step (c) a part of the SCAM separated in step (b) can be returned to step (a); however, if the HRT of step (a) is sufficiently long, e.g. more than 6 hours, return of part of the SCAM to step (a) can be dispensed with. Another part of the SCAM containing MSC—or all of it—can be harvested and valorised.

The biological oxidation of ammonia step (d) may be any oxidation reaction in which microorganisms (bacteria, archaea, etc.) convert ammonia to nitrogen species of higher oxidation state including oxidation state 0 (elemental), while alkaline species are converted to neutral or acidic species, thereby converting bicarbonate ions ($HCO_3^-$) to gaseous carbon dioxide. This includes bioreactions converting ammonia to nitrogen gas, nitrite and/or nitrate in one or more stages.

The effluent of step (a) will contain ammonia in the form of ammonium bicarbonate. Converting all ammonium fully to $N_2$ gas would liberate the $CO_2$ according to the following simplified equation:

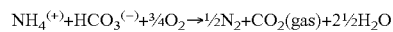

Converting 50% of the ammonium to nitrite would also liberate the $CO_2$ according to:

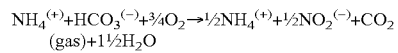

In case more than 50% of the ammonium would be oxidised to nitrite, the pH would drop significantly to below pH 7 unless also other pH buffering salts are present such as for example sodium bicarbonate. In that case more $CO_2$ could be released by further oxidation of ammonium to nitrite or nitrate.

It is preferred to predominantly convert ammonia to harmless molecular nitrogen. This can be done by partial oxidation of ammonia to nitrite and then converting the nitrite with remaining ammonia to molecular nitrogen, using microorganisms capable of oxidising ammonia to nitrite in the presence of oxygen (sometimes referred to as "nitritifiers", typically of the genera *Nitrosomonas* or *Nitrosococcus* among others) and microorganisms capable of converting ammonia to molecular nitrogen in the presence of nitrite (referred to as Anammox microorganisms, which are typically Planctomycetes of the genera *Brocadia, Kuenenia, Anammoxoglobus, Jettenia* among others). Advantageously, the microorganisms capable of oxidising ammonia to nitrite are present on the outer rim of microbial granules and the microorganisms capable of converting ammonia to molecular nitrogen (Anammox) are present in the core of the granules. In many instances, bacteria which oxidise nitrite to nitrate ("nitratifiers", typically of the genus *Nitrobacter*, but also *Nitrospira* and others) are undesired and these bacteria can be suppressed in the reactor, e.g. by applying a low non-granular sludge retention time (NGSRT), in particular of less than three times or even less than two times the HRT.

In the embodiment of step (d) using nitritifiers and Anammox microorganisms, a hydraulic retention time (HRT) between 0.2 and 2 days and a retention time for granular sludge of at least 6 times the HRT and a retention time for non-granular sludge of no more than 3 times the HRT are preferably maintained in step (d). The concentration of dissolved oxygen in step (d) is preferably from 0.4 to 4 mg/l, more preferably from 1.0 to 3.0 mg/L. The pH in step (d) is kept in a range between pH 6 and pH 8 preferably between 6.5 and 7.5. The temperature maintained in step (d) can be between 5 and 45° C., more preferably between 10 and 40° C., most preferably between 20 and 35° C. and can be essentially the same as the temperature of step (a). Nutrients may have to be added in step (d), in particularly nutrients such as phosphorus which have been limiting in step (a). Further details of this ammonia-oxidising process can be found e.g. in WO 00/05176, EP 2163525 and WO2014/171819.

Besides the oxidation of ammonia, also residual RBCOD and OBCOD can be simultaneously oxidised in step (d), which results in additional carbon dioxide production. In a preferred embodiment, step (a) results in RBCOD-depleted wastewater to be fed to step (d), which has a ratio of biodegradable COD (expressed as oxygen) to ammonia (expressed as N) of less than 1 on weight basis.

An important step of the present process is step (e) of transferring carbon dioxide liberated in step (d) to step (a). The production of gaseous $CO_2$ is driven by the air supply of step (d). Preferably the air supply in step (d) is controlled in such a way that (i) the dissolved oxygen level as indicated above is achieved and (ii) the gas exiting step (d) and the corresponding reactor is substantially reduced in oxygen, while containing significant levels, e.g. at least 2 vol. % of $CO_2$. The amount of air supplied can also be controlled by measuring and applying set points for one or more, but not limited to, other parameters such as dissolved ammonium concentration, dissolved nitrite concentration, dissolved nitrate concentration, pH and $CO_2$ concentration in the off-gas. The $CO_2$-containing gas originating from step (d) may constitute, or may be added to, the air used for aeration of step (a), or it may be introduced separately. A part of the liberated $CO_2$ will remain in solution as dissolved $CO_2$ in the effluent of step (d). Additional recycling of liquid effluent from step (d) to step (a) can therefore be advantageous in further reducing the pH in step (a).

The MSC-loaded activated sludge and/or grown activated sludge harvested in step (f) has a high MSC content, in particular of at least 50%, by weight. Preferably, it contains at least 60%, more preferably at least 70%, most preferably at least 80% MSC based on dry weight of the organic part of the sludge. The Microbial Storage Compound (MSC) in particular comprises one or more polyhydroxyalkanoates (PHA).

In many types of wastewater that can be used as feed for the present process, the level of RBCOD is relatively low, which can be a disadvantage when a high production of MSC is desired. The level can advantageously be increased by incorporating a process step, preceding step (a), of anaerobically fermenting the wastewater to increase the level of RBCOD, in particular volatile fatty acids ($C_1$-$C_6$), medium-chain fatty acids ($C_7$-$C_{12}$), lactate, glycerol and/or ethanol. Thus, the process may comprise a preceding step in which the raw wastewater is subjected to hydrolysis and/or fermentation in a separated reactor, for example an anaerobic reactor in which partial fermentation (hydrolysis, acidogenesis, acetogenesis) is achieved. Advantageously, also during this step, part of the nutrients, in particular phosphorus, present in the wastewater is removed, thus lowering the nutrient to RBCOD ratio. If needed, phosphorus may alternatively or additionally be reduced by addition of magnesium to produce struvite and separating the struvite precipitate.

The invention also pertains to a reactor system for treating wastewater containing RBCOD and ammonia, comprising
at least one first reactor having aerating means at the bottom, an inlet for raw wastewater, an inlet for nutrients, at least one gas inlet at the bottom, a gas outlet at the top, an liquid effluent outlet at the top and a pH meter for measuring the pH of the reactor content;
a first separator, inside or outside the first reactor, connected to the liquid effluent outlet of the first reactor(s) for separating solids from the effluent of the first reactor(s), with a solids outlet and a liquid outlet;
a second reactor having aerating means at the bottom, a liquid inlet connected to the liquid outlet of the first separator, an inlet for nutrients, a gas inlet with aeration means at the bottom, a gas outlet at the top, an liquid effluent outlet at the top, the gas outlet being connected to a gas inlet of the first reactor(s) via a controllable valve which controls the flow of the gas fed from the second reactor to the first reactor on the basis of the pH measured by the pH meter of the first reactor(s);
a second separator, inside or outside the second reactor, connected to the liquid effluent outlet of the second reactor for separating granular solids from the effluent of the second reactor, with a solids outlet and a liquid outlet, with a solid line from the second separator to the second reactor for returning granular solids to the second reactor;
and preferably a liquid line connecting the liquid outlet of the second separator to the inlet for raw wastewater of the first reactor via a controllable valve which controls the flow of the liquid fed from the second reactor to the first reactor.

DETAILED DESCRIPTION OF THE DRAWING

The appending FIGURE illustrates an embodiment of the present process and apparatus. It shows an RBCOD-containing influent 1 and a treated effluent 2, and optionally a partly treated effluent 3. Influent 1 is fed into an aerobic reactor (or set of reactors) 10, containing storage compound-accumulating microorganisms (SCAM). Air can be supplied through aeration means 11. Spent air from reactor 20 containing carbon dioxide and oxygen is supplied through 24 and spent air from reactor 10 is vented through 12 and possibly post-treated. Nutrients can be supplied through inlet 19. The reactor (or each reactor if there is more than one) is provided with a pH meter (not shown) for measuring the pH of the reactor content. Effluent 13 from reactor(s) 10 is separated in separator 15, the resulting clarified liquid being fed to ammonia-oxidising reactor 20 through line 14; a part of it may be discharged through line 3 without passing through reactor 20. Sludge separated in separator 15 through line 16 is partly returned to aerobic reactor 10 through line 17 and partly carried off through line 18 for harvesting and processing of the enriched SCAM.

The ammonia-oxidising reactor 20 is provided with controllable aerating means 21. Nutrients can be supplied through an additional inlet (not shown). Spent air, containing carbon dioxide, is collected through line 22 and partly carried off through vent 23 and partly fed to aerobic reactor 10 through line 24 in a controlled manner, i.e. under control of a signal issuing from the pH meter arranged in reactor 10. Reactor 20 can be provided with one or more analysers (not shown) for measuring pH, ammonia level, nitrite level or nitrate level in the reactor content or the $CO_2$ level in the off-gas, and the measured data can be used for controlling the air supply through 21. Effluent 26 from reactor 20 is separated in separator 25, the resulting clarified liquid 27 being partly or wholly discharged as treated effluent 2 and partly returned to aerobic reactor 10 through line 28 in the event of excessive nitrogen load of influent 1 or for further dissolved $CO_2$ supply. Non-granular sludge separated in separator 25 is carried off through line 29. Granular sludge separated off in separator 25 (or elsewhere, e.g. in an internal separator of reactor 20) is collected in line 31 and partly returned to reactor 20 through line 32 and partly carried off through line 33.

EXAMPLES

Example 1

A condensate stream of 100 m³/h from a municipal sludge drying unit contains 100 mmol/l $NH_4$ (10 kmol/h=140 kg N/h), 60 mmol/l acetate (6 kmol/h=354 kg acetate/h, equivalent to 384 kg/h RBCOD), 20 mmol/l $HCO_3$ (2 kmol/h), 10 mmol/l Na and less than 0.02 mmol/l P (<2 mol/h=62 g P/h) at a pH of 9.0. In the calculations provided for this example it is assumed that there is no OBCOD present in the condensate stream. The stream is introduced into a bioreactor having an effective volume of 300 m³ to produce 3.9 ton/day dry solids biomass containing 80 wt. % PHA by aerating and limiting the amount of phosphate supplied to 0.7 kg P/h (RBCOD:P≈550:1). The reactor is kept at pH 8.6 by recycling 1500 Nm³/h off gas from an Anammox reactor arranged downstream of the PHA bioreactor containing 4.6% $CO_2$ and 16% $O_2$ and by recycling 50 m³/h liquid effluent from the Anammox bioreactor back to the PHA reactor. The resulting HRT is 2 h. Additionally 200 m³ of fresh air is supplied and controlled on the basis of dissolved oxygen concentration. The resulting pH in the PHA reactor is 8.6 with 0.65% $CO_2$ and 12.7% oxygen in the off gas. In the PHA reactor, 4.6 kmol/h $CO_2$ is produced along with the conversion of acetate to PHA, 3.1 kmol/h $CO_2$ is recycled with the 1500 Nm³/h off gas from the Anammox reactor and 0.7 kmol/h $CO_2/HCO_3$ is recycled to the PHA reactor by means of the 50 m³/h liquid effluent recycle from the Anammox reactor.

From the 150 m³/h liquid effluent of the PHA bioreactor, 100 m³/h is treated in an 800 m³ Anammox bioreactor (HRT=8 h). The Anammox reactor is aerated by supplying 2500 Nm³/h air. Granular sludge containing Anammox bacteria is continuously recycled to the Anammox reactor and a small amount of sludge is discharged in order to sustain a GSRT of about 30 days. Small amounts of nutrients containing P and other essential growth elements are supplied to the Anammox reactor. As a result of the Anammox reaction, the pH in the reactor drops to pH 7.0 and the reactor is controlled at an output of 1 mmol/l residual ammonium concentration by controlling the amount of air supplied. Overall in the process 66% of the ammonia is converted to nitrogen gas resulting in sufficient $CO_2$ liberated to keep the pH in the upstream PHA reactor at pH 8.6. Temperature in both reactors is kept at 30 degrees Celsius.

Example 2

PHA production from a high ammonia and volatile fatty acid (VFA) containing condensate was demonstrated at lab scale using gaseous carbon dioxide for pH control. A continuous set-up including two double walled glass reactors was operated for more than two months. The system consisted of a PHA accumulation reactor, a settler and a growth reactor. Condensate was pumped continuously to the PHA accumulation reactor and effluent was sent to the settler. The overflow of the settler consists of the treated VFA-depleted condensate. A part of the underflow from the settler (sludge) was pumped to the growth reactor and another part of the sludge was discharged. The level in the growth reactor was kept constant and excess water with sludge was pumped back to the PHA accumulation reactor. Nutrients essential for growth including phosphate were added to the growth reactor. The following settings were applied:

PHA accumulation reactor (1): 3.5 litre volume, temperature controlled at 30° C., pH controlled at pH 8.5 using an additional supply of carbon dioxide, aeration using air ensuring a dissolved oxygen concentration above 20% saturation.

Feed flow to the PHA reactor: 0.6 l/h of condensate with a pH of 9 and a bicarbonate alkalinity of 75 mmol/l containing 1700 mg/l ammonia, 540 mg/l acetate, 510 mg/l propionate, 880 mg/l butyrate, 470 mg/l isobutyrate, 510 mg/l valerate, 740 mg/l isovalerate and 83 mg/l caproate. The total dissolved COD concentration was measured at 7.9 g/l with an estimated RBCOD concentration based on the VFA specified of 6.6 g/l. Conductivity was 8.6 mS/cm and phosphorus was below 0.5 mg/l P. A small amount of a concentrated solution containing NaCl, KCl, $CaCl_2$ and $MgCl_2$ was directly added to the reactor in order to arrive at 80 mg/l Na, 25 mg/l K, 25 mg/l Mg and 50 mg/l Ca.

Settler: 10 cm diameter with conical bottom

Growth reactor: 1.3 litre volume, temperature controlled at 30° C., pH controlled at pH 8.5 using an additional supply of carbon dioxide and aerated using air ensuring a dissolved oxygen concentration above 20% saturation. Pulse addition every 15 minutes of a commercial Nutrient mixture containing P (as $H_3PO_4$) and trace metals, where P is the limiting compound. Every pulse 2.7 mg of P is added.

Sludge discharge from settler: 0.08 l/h

Sludge recycle from settler to the growth reactor and from the growth reactor back to the PHA accumulation reactor: 1.2 l/h.

The system characteristics are as follows:

Hydraulic retention time in the PHA accumulation reactor: 1.9 hours

Hydraulic retention time in the growth reactor: 1.1 hours

Average sludge retention time (SRT): around 48 hours

Ratio P added in the growth reactor: RBCOD in Feed in weight: 1/366

RBCOD loading rate to the PHA reactor: 27 kg/m³·d

When starting the system under the above conditions the reactors were seeded with sludge already containing a mixture of PHA accumulating organisms taken from another lab reactor fed with a synthetic sodium acetate solution and controlled at pH 8.5 and 30° C. The other lab reactor was originally seeded with aerobic sludge from a municipal wastewater treatment plant.

Under these conditions a steady-state was achieved after a few weeks. It was confirmed by analysis that normally the residual concentrations of all volatile fatty acids in the PHA accumulation reactor and the settler overflow was below 100 mg/l and that residual dissolved COD was around 1 g/l. PHA content was analysed in samples taken from both the PHA accumulation reactor and the growth reactor. The PHA content in the sludge in the PHA accumulation reached 52 wt. % based on organic content whereas the PHA content in the growth reactor was a few percent lower (around 48 wt. %).

The invention claimed is:

1. A process for producing a microbial storage compound (MSC) from a feed stream comprising biodegradable chemical oxygen demand (RBCOD) at a level of at least 250 mg/l, and ammonia at a level which is at least 0.2 g N per g RBCOD, the process comprising:
   (a) subjecting the feed stream to storage compound-accumulating microorganisms (SCAM) in the presence of dissolved oxygen, while adding carbon dioxide as necessary for maintaining a pH below 9, in one or more stages, to produce SCAM which contain MSC at a level of at least 50 wt. % based on dry weight of the organic part of the microorganisms, and RBCOD-depleted wastewater;
   (b) separating at least a part of the SCAM containing MSC produced in step (a) from the RBCOD-depleted wastewater;
   (c) optionally returning a part of the SCAM separated in step (b) to step (a),
   (d) subjecting at least a part of the RBCOD-depleted wastewater to ammonia-oxidising microorganisms (AOM) in the presence of dissolved oxygen to produce RBCOD-depleted and ammonia-depleted wastewater, and a gas containing carbon dioxide;
   (e) feeding at least a part of the gas containing carbon dioxide from step (d) to step (a); and
   (f) harvesting at least a part of the SCAM separated in step (b).

2. The process according to claim 1, in which the amount of gas containing carbon dioxide fed to step (a) from step (e) is controlled based on a set point for pH in step (a).

3. The process according to claim 1, wherein the AOM comprise microorganisms capable of oxidising ammonia to nitrite in the presence of oxygen and microorganisms capable of converting ammonia to molecular nitrogen in the presence of nitrite.

4. The process according to claim 3, wherein step(d) is carried out using microbial granules comprising a core and an outer rim, wherein the microorganisms capable of oxidising ammonia to nitrite are present on the outer rim of microbial granules and the microorganisms capable of converting ammonia to molecular nitrogen (Anammox) are present in the core of the granules.

5. The process according to claim 4, wherein a hydraulic retention time (HRT) between 0.2 and 2 days and a retention time for granular sludge of at least 6 times the HRT and a retention time for non-granular sludge of less than 3 times the HRT are maintained in step (d).

6. The process according to claim 1, wherein a part of the RBCOD-depleted and ammonia-depleted wastewater produced in step (d) is recycled to step (a) so as to reduce the concentration of ammonia and further lower the pH by increasing the level of dissolved carbon dioxide returned to step (a).

7. The process according to claim 1, wherein the RBCOD-depleted wastewater produced in step (a) has a ratio of biodegradable COD (expressed as oxygen) to ammonia (expressed as nitrogen) of less than 1.0.

8. The process according to claim 1, wherein step (a) involves a total sludge retention time (SRT) of between 12 and 72 h.

9. The process according to claim 1, wherein the feed stream supplied in step (a) contains phosphorus, and wherein the weight ratio, on element basis, of phosphorus to RBCOD-carbon (Pa1/Ca) is below 1/100.

10. The process according to claim 1, wherein step (a) comprises two reactor stages wherein in the first stage (a1) the feed stream is subjected to SCAM in the presence of dissolved oxygen and with limitation of phosphorus or another nutrient which is essential for growth so as to reduce the level of RBCOD, and in the second stage (a2) downstream of stage (a1) phosphorus and/or another nutrient which is essential for growth is supplied to the stream having a reduced RBCOD content; wherein stages (a1) and (a2) are operated in series, or stage (a2) is operated as a return side stream.

11. The process according to claim 10, wherein, in stage (a2), the weight ratio, on element basis, of phosphorus supplied in step (a) divided by the amount of RBCOD-carbon supplied in stage (a1) (Pa2/Ca) is between 1/60 and 1/500, or a corresponding level for another element essential for growth.

12. The process according to claim 10, wherein the hydraulic retention time (HRT) of stage (a1) is between 0.5 and 8 h and the HRT of stage (a2) is between 0.1 and 6 h.

13. The process according to claim 1, further comprising:
(g) isolating MSC from the harvested SCAM.

14. The process according to claim 1, in which the at least part of the SCAM containing MSC is separated from the RBCOD-depleted wastewater in step (b) as a sludge, the sludge containing at least 60% MSC based on dry weight of the organic part of the sludge.

15. The process according to claim 14, in which the sludge contains at least 70% MSC based on dry weight of the organic part of the sludge.

16. The process according to claim 1, in which the microbial storage compound (MSC) comprises a polyhydroxyalkanoate (PHA) and wherein the storage compound-accumulating microorganisms (SCAM) comprise PHA-accumulating microorganisms.

17. The process according to claim 1, which is preceded by a step of anaerobically fermenting the feed stream to increase the level of RBCOD.

18. The process according to claim 1, which is preceded by a step of anaerobically fermenting the feed stream to increase the level of volatile fatty acids, medium-chain fatty acids, lactate, ethanol and/or glycerol.

* * * * *